US009688952B2

(12) United States Patent
Schaefer

(10) Patent No.: US 9,688,952 B2
(45) Date of Patent: Jun. 27, 2017

(54) MICRO FLUID DOSING UNIT AND TESTING DEVICE FOR BIOMATERIAL

(71) Applicant: Buerkert Werke GmbH, Ingelfingen (DE)

(72) Inventor: Peggy Schaefer, Schoental (DE)

(73) Assignee: Buerkert Werke GmbH, Ingelfingen (DE)

( * ) Notice: Subject to any disclaimer, the term of this patent is extended or adjusted under 35 U.S.C. 154(b) by 348 days.

(21) Appl. No.: 14/325,892

(22) Filed: Jul. 8, 2014

(65) Prior Publication Data

US 2015/0017713 A1 Jan. 15, 2015

(30) Foreign Application Priority Data

Jul. 8, 2013 (DE) .................... 20 2013 103 016 U

(51) Int. Cl.
*C12M 1/34* (2006.01)
*C12M 1/26* (2006.01)
(Continued)

(52) U.S. Cl.
CPC ................ *C12M 33/12* (2013.01); *B01J 4/02* (2013.01); *B01J 19/0093* (2013.01);
(Continued)

(58) Field of Classification Search
CPC ...... C12M 23/12; C12M 23/16; C12M 23/40; C12M 23/44; C12M 29/14; C12M 29/18; C12M 33/12; B01J 4/02; B01J 19/0093; B01L 3/502753; B01L 2400/0487; B01L 2400/0638
See application file for complete search history.

(56) References Cited

U.S. PATENT DOCUMENTS 7,976,795 B2 * 7/2011 Zhou ..................... B01L 3/5025
422/500
2005/0260745 A1 11/2005 Domansky et al.
2011/0275058 A1 11/2011 Zhou et al.

FOREIGN PATENT DOCUMENTS

DE 2821801 B2 10/1980
DE 60128955 T2 2/2008
(Continued)

OTHER PUBLICATIONS

German Office Action issued on May 3, 2016 corresponding to German Application No. 102014109187.6 citing the above reference(s).

(Continued)

*Primary Examiner* — William H Beisner
(74) *Attorney, Agent, or Firm* — Hauptman Ham, LLP

(57) ABSTRACT

A micro fluid dosing unit includes a test container containing biomaterial needing oxygen. The test container has at least one first container which contains water and at least one second container which contains a pharmacological substance, wherein the first and the second containers have a container outlet leading to the test container and are mounted on a common valve carrier plate containing control channels, which includes control channel ports for control valves to be coupled thereto. In the valve carrier plate a separate valve control chamber is formed for each container, which is sealed by a membrane, wherein associated container outlets are opened and closed by the membrane movement.

19 Claims, 3 Drawing Sheets

(51) Int. Cl.
  *B01J 4/02* (2006.01)
  *B01J 19/00* (2006.01)
  *B01L 3/00* (2006.01)
  *C12M 1/32* (2006.01)
  *C12M 1/00* (2006.01)

(52) U.S. Cl.
  CPC ....... *B01L 3/502746* (2013.01); *C12M 23/12* (2013.01); *C12M 23/40* (2013.01); *C12M 29/00* (2013.01); *B01J 2219/00894* (2013.01)

(56) References Cited

FOREIGN PATENT DOCUMENTS

| | | |
|---|---|---|
| DE | 102007028116 B3 | 11/2008 |
| DE | 102008028772 A1 | 12/2009 |
| DE | 202012003948 U1 | 5/2012 |
| WO | 0078456 A1 | 12/2000 |

OTHER PUBLICATIONS

German Search Report dated Feb. 3, 2014, citing the above reference(s).

* cited by examiner

MICRO FLUID DOSING UNIT AND TESTING DEVICE FOR BIOMATERIAL

CROSS REFERENCE TO RELATED APPLICATION

This application claims priority of German Patent Application No. 20 2013 103 016.3, filed on Jul. 08, 2013 in the German Patent and Trade Mark Office, the disclosure of which is incorporated herein in its entirety by reference.

FIELD OF THE INVENTION

This invention relates to a micro fluid dosing unit and a testing device for biomaterial.

BACKGROUND

The term "biomaterial" refers to uni- or multicellular living organisms, in particular microorganisms, which live in an aqueous environment with oxygen content. Such organisms are increasingly used to check the effect of pharmacological substances on living organisms in a testing device. Such tests replace tests on mammals.

Especially microorganisms floating in water, however, require a permanent minimum flow of the water, so as not to stick to the test container wall and keep moving. The test containers at best have a size of few cubic millimeters, so that the dosage of the flow rate and flow velocity of the fluid as well as the exactly dosed addition of the pharmacological substances to be tested is problematic.

The invention creates a micro fluid dosing unit for such testing device as well as a testing device itself, which is simplified.

SUMMARY

The micro fluid dosing unit according to the invention comprises at least one first container, which contains water, and at least one second container, which contains a pharmacological substance. The first and the second containers have a container outlet leading to a test container and are mounted on a common valve carrier plate containing control channels. The valve carrier plate includes control channel ports for control valves to be coupled thereto, wherein for each container a separate valve control chamber is formed in the valve carrier plate, which is sealed by a membrane. Via the membrane movement, the associated container outlets are opened and closed.

Preferably, there is provided at least one third container receiving recycling liquid, which is mounted on the valve carrier plate and for which the valve carrier plate includes a separate valve control chamber actuatable by a control valve, which is sealed by a membrane, and wherein the container outlet of the third container is opened and closed by the membrane movement.

While in the prior art expensive individual units are coupled with each other via hose connections or tube connections, the invention provides a distinctly simplified construction for this purpose, in that at least the first, the second and the third container are mounted on a common valve carrier plate. In this valve carrier plate valves are designed in a simple way, in that for each container a separate, pneumatically actuatable valve control chamber is formed. This valve control chamber can easily be manufactured by drilling or milling out or during injection or injection molding of the valve carrier plate. A membrane closing the valve control chamber acts as valve body for opening and closing the associated container outlets. The dosing unit according to the invention is a compact unit. The membrane valves permit small amounts of fluid control.

Preferably, all containers are accommodated in a common housing, so that the compactness can still be increased.

At the housing, at least one valve chamber with a valve seat against which the associated membrane rests in the closed position can be formed for each container. In the open position, the fluid thus can flow out through the distributor chamber or, more generally, flow through the chamber. It should be emphasized that the distributor chamber faces the associated valve control chamber and both chambers are separated by the membrane. By deflection of the membrane for example in direction of the distributor chamber, the volume of the valve control chamber is increased, and the valve control chamber then also extends into the housing. This can of course also be effected the other way round, when the membrane bulges into the valve control chamber. The volume of the distributor chamber then slightly increases, and the same protrudes into the valve carrier plate.

The design of the dosing unit can be reduced, when a common outlet channel leading away from the first to the second container, towards the test container, is provided, which is coupled with the distributor chambers of the first and the second containers. Thus, the common outlet channel is produced via only one bore in the valve carrier plate.

The pharmacological substances need not necessarily be disposed of immediately after having flown through the test container. It is also possible and even advantageous to reuse this pharmacological material. For this purpose, a return line coming from the test container and leading to the third container is employed, to which a separate valve control chamber in the valve carrier plate is associated. This means that the pharmacological material is transferred into the third container in a valve-controlled manner.

From this third container the pharmacological material can flow over into the second container.

The dosing unit is simplified in construction when between the housing or housings of the containers on the one hand and the valve carrier plate on the other hand a common membrane for all distributor chambers is provided. The membrane hence is a thin flexible plate placed or clamped inbetween.

The dosed addition of the fluid must be effected very precisely even at smallest flow rates. This dosage is effected in that into the first and second containers each in the region of its upper end compressed gas, namely compressed gas dosed exactly to a certain pressure, is introduced. Via this adjusted pneumatic pressure of the gas or air cushion produced above the liquid surface, the liquid quantity flowing out of the individual containers is controlled exactly. For this purpose, the containers are closed on their upper side. This can be effected for example by one common or several individual membranes, which is/are simply clamped between a lid and the containers.

Each container has its own compressed gas control line which opens into the same, preferably in the region of its upper side. To each compressed gas control line a separate control valve is associated, via which the compressed gas supply into the container is opened or closed.

The construction of the dosing unit is again simplified when the compressed gas control lines pass over into channels in the valve carrier plate, which have ports to associated, preferably separate control valves. This means that the control valves controlling the compressed gas flow also are mounted on the valve carrier plate, which control valves have their own ports to associated, separate control valves. This means that the control valves for the compressed gas also are mounted on the valve carrier plate.

The pressure of the compressed gas must be set very exactly, so that the dosing quantity likewise can be controlled very exactly. For this purpose, a common proportional valve is provided for the compressed gas flowing to the containers. Preferably, there is a common proportional valve for compressed gas which flows to all containers. It is not absolutely necessary that the flow velocity of water and pharmacological substance is different, but rather their velocity should be the same. For this reason, the pressure of the compressed gas which presses the fluid out of the respective container also must be the same. Hence, a single proportional valve is sufficient according to one embodiment of the invention.

In addition, there is preferably provided a pneumatic compressor for the compressed gas and/or the control air for the valves. In particular, this can also be a common pneumatic compressor.

As common construction unit, pneumatic compressor and proportional valve can be part of a pneumatic block which is sealed to the outside by a housing. This pneumatic block then is coupled with the valve carrier plate via a small number of tubings.

The outlet channel merely has a diameter of 0.04 to 0.08 mm, preferably about 0.06 mm, in order to realize the small flow rate.

The dosing unit is controlled such that a flow rate between 0.5 and 10 µl of liquid per minute is realized.

An easy manufacture of the channels in the valve carrier plate for example is effected in that the channels are open on the end face of the valve carrier plate, so that they are drilled into the end face from outside. The control valves then can releasably be mounted on the end faces and here couple to the channels.

The testing device according to the invention with a test container receiving biomaterial and a micro fluid dosing unit according to the invention is designed such that between the micro fluid dosing unit and the test container the fluid, i.e. the water or the pharmacological substance, flows without use of a pump. Due to differences in height and/or the compressed air the flow is produced on the liquid surface in the container. Since the biomaterial needs oxygen to live, no pump is interposed, as pumps would completely deprive the liquid of oxygen.

DETAILED DESCRIPTION

Figure 1:
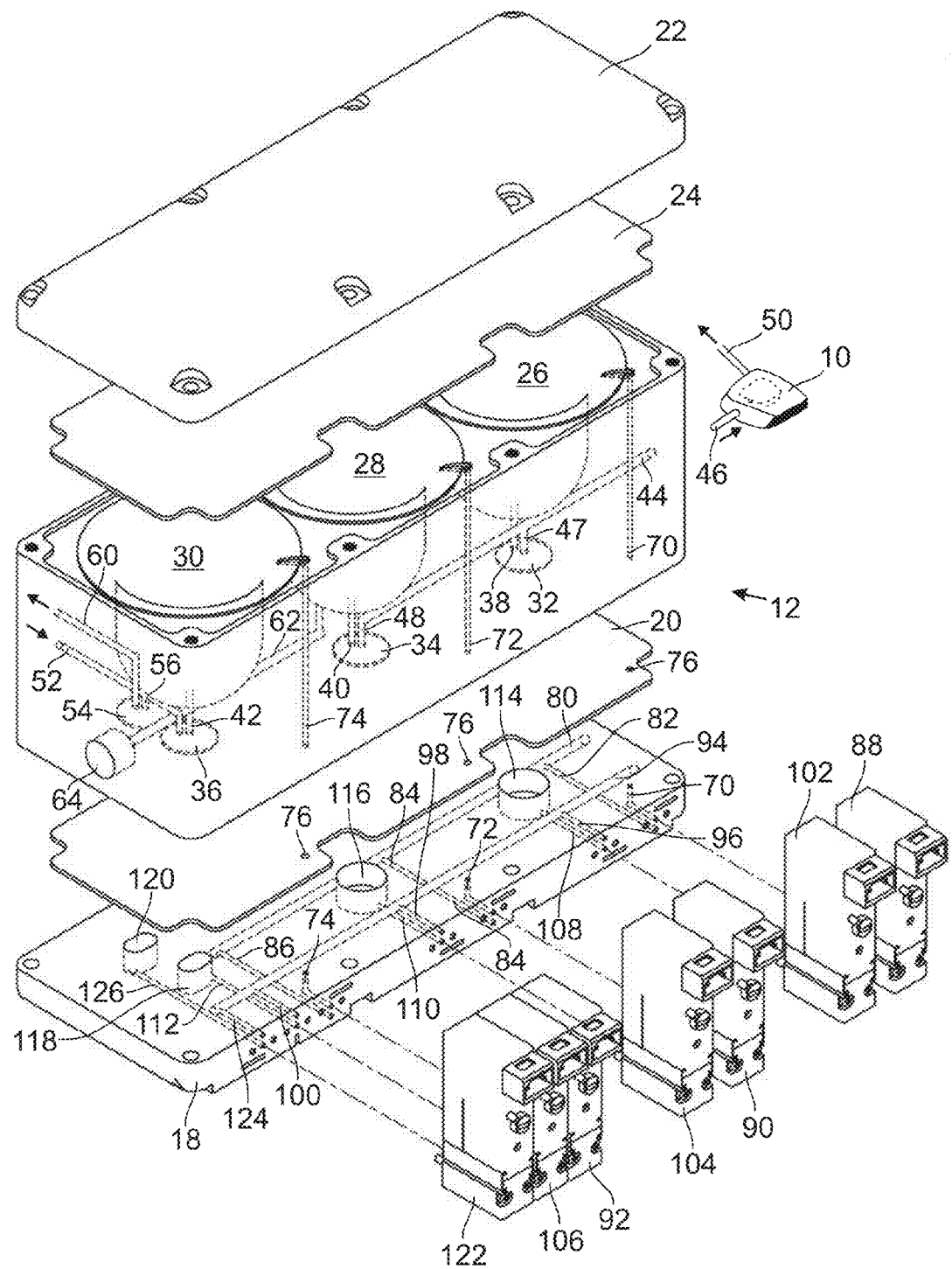
FIG. 1 shows an exploded view of a part of a testing device for biomaterial according to the invention with a micro fluid dosing unit according to the invention.

FIG. 1 shows a part of a testing device with a test container 10 in which biomaterial in the form of uni- or multicellular microorganisms is accommodated. These microorganisms live in water and need oxygen. On these microorganisms pharmacological substances are tested.

Figure 4:
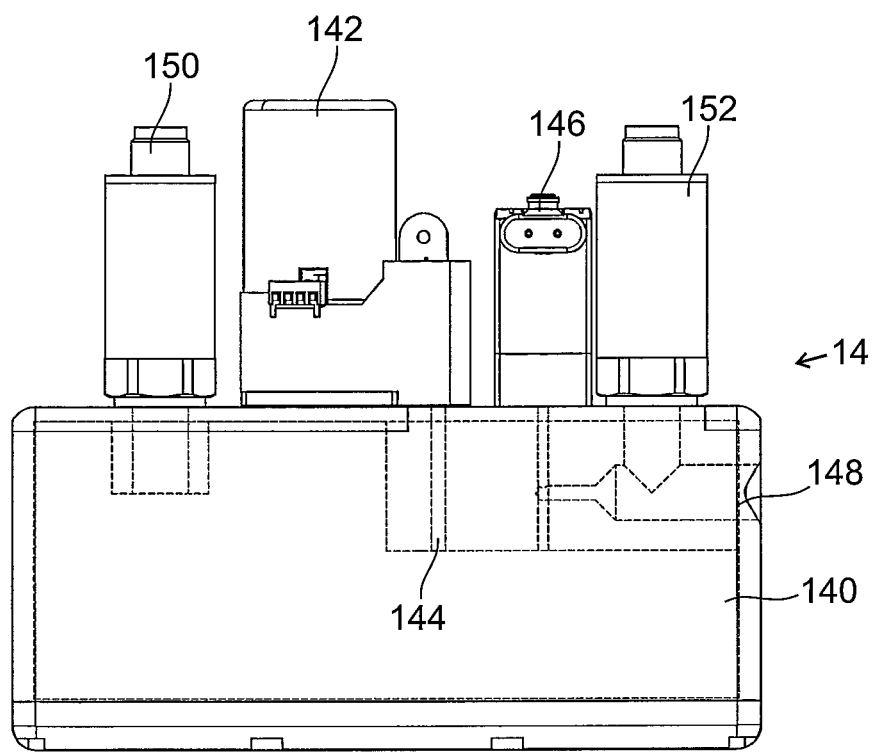
FIG. 4 shows a pneumatic block as part of the micro fluid dosing unit according to the invention in a side view.

Beside the test container 10, the device comprises a so-called dosing block 12 which consists of several individual parts and is shown in FIG. 1 as well as a pneumatic block 14 connected to the dosing block 12, which is shown in FIG. 4.

In the following, the dosing block 12 according to FIGS. 1 to 3 will be described in detail.

The dosing block 12 comprises a housing 16 which accommodates several liquid containers, a valve carrier plate 18 on which several control valves are mounted, a membrane 20 clamped between valve carrier plate 18 and housing 16, a lid 22 closing the containers at the top as well as a membrane 24 clamped between lid 22 and the containers and the housing 16, which serves for sealing.

The housing 16 can be made of plastics, for example, i.e. be an injection-molded part, and can be designed as disposable, i.e. one-way article, whereas lid 22, valve carrier plate 18 and switching valves are no disposable articles, as they do not get in contact with pharmacological material.

The housing 16 includes a first container 26 in which water is received, a second container 28 in which a pharmacological substance dissolved in water is accommodated, and a third container 30 into which recycling liquid flows, which is recirculated from the test container 10 to the dosing block 12.

The containers 26 to 30 can be designed as cavities open at the top in the possibly integrally formed housing 16 and need not necessarily be manufactured as separate parts.

In the bottom of the housing 16 or in an adjoining part, which is mounted on the housing 16 and possibly also can be part of the housing, separate distributor chambers 32 to 36 are provided for each container 26 to 30. The distributor chambers 32 to 36 are cavities open at the bottom, which at the bottom are sealed in a fluid-tight manner by the common membrane 20.

Channels small in cross-section open into these distributor chambers 32 to 36, proceeding from the respective bottom of the containers 26 to 30, so-called container outlets 38 to 42. These container outlets 38 to 42 should start at the deepest point of the respective container 26 to 30.

The container outlets 38 to 42 so to speak end at the ceiling wall of the respective distributor chamber 32 to 36 opposite the membrane 20.

Beside the container outlet 38 to 42, an outlet channel starts in each distributor chamber 32 to 36. The first container 26 and the second container 28 have a common outlet channel 44, which via a line 46 coupled with the housing 16 is in flow connection with the test container 10. The common outlet channel 44 has two short stub lines 47, 48, which each end beside the orifices of the container outlets 38, 40 in the distributor chamber 32, 34.

The wall facing the membrane 20, more exactly the end-face wall of the distributor chambers 32, 34, forms a valve seat against which the membrane 20 can press when it is pressed in direction of the distributor chamber 32, 34. The container outlet 38 and/or 40 to the stub line 47, 48 hence can each be closed and opened individually.

From the test container 10 a return line 50 leads back to the housing 16.

The return line 50 is coupled to a return channel 52 provided in the housing 16, which ends in a further distributor chamber 54 and in addition at the distributor chamber 36.

The distributor chamber 54 likewise is closed by the membrane 20 and has a corresponding valve seat on its upper side, i.e. ceiling wall, facing the membrane 20.

Starting from the distributor chamber 36 a container inlet channel 42 is provided, which opens into the container 30. This container inlet channel 42 like the return line 52 can be closed by the membrane 20.

Via the connecting channel 56, which leads from the return line 52 into the distributor chamber 54, the medium can be guided out of the system, when the membrane 20 does not rest against the valve seat of the distributor chamber 54. The connecting channel then is open with the outlet channel 60. The container inlet channel 42 is closed in this condition.

An additional, not valve-switched connecting channel 62 brings the containers 28, 30 in flow connection. The connecting channel 62 starts and ends at the bottom of the respective containers 28, 30.

The connecting channel 62 like the remaining channels is produced by drilling, here by horizontal drilling. At the end-face outlet of the housing 16, the connecting channel 62 is closed by a closure 64.

As already explained above, the containers 26 to 30 are closed at the top, namely by the membrane 24.

In the region of the upper side of the containers, however, a separate compressed-gas control line 70 to 74 opens into each of the containers 26 to 30, which extends vertically through the housing 16 and further through openings 76 in the membrane into corresponding channels in the valve carrier plate 18.

In the valve carrier plate 18, the control lines 70 to 74 are bent by preferably 90°, in order to open into ports on one end face.

In the following, the channels, lines or chambers in the valve control plate 18 will be explained. For all three containers 26 to 30, there is a common compressed gas supply line 80 which then leads via channels 82 to 86 and end-face control channel ports to control valves 88 to 92 coupled thereto.

The control valves 88 to 92 are coupled to the end face of the valve carrier plate 18 and switch the channels 82 to 86 to their associated compressed gas lines 70 to 74 on or off.

Beside the compressed gas supply line 80, the valve carrier plate 18 also has a central compressed gas supply line 94 which serves for switching the individual membrane valves formed by the distributor chambers 32 to 36.

Starting from the compressed gas supply line 94 a channel 96, 98 and 100 each associated to a single container 26 to 30 is provided, which then likewise ends in a port on the end face and to which a control valve 102, 104, 106 each is coupled.

The control valves 102 to 106 serve for switching the membrane valves, which among other things are formed by the distributor channels 32 to 36.

From the valves 102 to 106 an associated channel 108, 110 and 112 each leads to an associated valve control chamber 114, 116, 118 in the valve carrier plate 18.

Each container 26 to 30 has its own valve control chamber 114 to 118, which faces the associated distributor chamber 32 to 36 and is separated from the same by the membrane 20.

The distributor chamber 54 can be switched separately and likewise has its own valve control chamber 120 in the valve carrier plate, wherein the valve control chamber 120 in turn is coupled with its own control valve 122. Corresponding channels 124, 126 lead from the compressed gas supply line 94 to the control valve 122 or from the control valve 122 to the valve control chamber 120.

The compressed gas supply line 80 is in flow connection with the pneumatic block 14 (see FIG. 4).

This pneumatic block 14 comprises a housing 140 in which several lines are provided and to which several units are coupled.

A pneumatic compressor 142 ensures a maximum pressure of the compressed air flowing into the valve carrier plate 18. Via a line 144 this maximum pressure flows to the compressed gas supply line 80.

The compressor 142 also supplies the compressed gas which flows to the compressed gas control lines 70 to 74. However, the pressure of this compressed gas is controlled exactly, namely via a proportional valve 146 which is interposed. The outlet 148 at which controlled compressed gas is present is coupled with the compressed gas supply line 94.

Pressure transmitters 150, 152 ensure that the pressure of the compressed gas is monitored and set exactly.

Switching of the respective membrane valves is effected in that the compressed gas coming from the compressor flows into the associated valve control chamber 114 to 120 with maximum pressure and an open valve 102, 104, 106 or 122 and in doing so partly presses the membrane 20 upwards into the associated distributor chamber such that the valve seat is closed.

In the following, the mode of operation of the micro dosing unit with its dosing block 12 and the pneumatic block 14 as well as the entire testing device will be explained.

In the test container 10, microorganisms are contained.

With a very small flow rate between 0.5 and 10 µl per minute water flows from the container 26 into the test container 10, in that the associated control valve 102 is switched to OPEN, so that the membrane 20 does not rest against the valve seat and the container outlet 38 is coupled with the stub line 47. Due to the minimum flow rate, the microorganisms are prevented from sticking to the chamber wall and the mobility of the microorganisms is maintained. Too large a flow rate might kill the microorganisms, which is not desired either.

The fluid flow between the containers 26 to 30 and the test container 10 is effected without interposition of pumps.

The flow rate for the respective fluid is controlled exclusively via the pressure inside the respective container 26 to 30, i.e. via the pressure in the air cushion produced above the fluid column in the container 26, 28.

When the flow rate must be increased, the proportional valve 146 is switched correspondingly and the associated valve 88 or 90 is actuated. To test the pharmacological effects of the pharmacological substance accommodated in the container 28, the corresponding valve 104 is actuated, so that the pharmacological substance can flow out of the container 28 into the outlet channel 44, in order to get from there into the test container 10.

When the corresponding valve 106 is switched to OPEN, the liquid (recycling liquid) flowing back gets into the container 30 via the distributor chamber 36. The valve 122 then is set to closing.

By applying a corresponding pressure in the air cushion in the container 30, the same can be transferred into the container 28. For this purpose, the overflow line 62 is used. The pressure in the container 28 should of course be reduced, in order to provide for this overflow.

When the system or only the container 30 should be emptied, the control valve 122 is actuated, so that the membrane 20 does not urge against the valve seat in the distributor chamber 54. The outlet line 60, which leads to an external waste container, hence is traversed by fluid. The container can be emptied, when medium flows out and into the line 60 via the container inlet 42.

When another pharmacological substance is to be tested or when the containers no longer can be cleaned sufficiently, the containers or the housing 16 integrally connected therewith only must be exchanged for a new container, so that the device and the micro fluid dosing unit are very cost-efficient to maintain.

The containers are designed for a volume of about 25 ml.

The pressure in the compressed gas supply line 94 is 0.08 to 1 bar.

Figure 2:
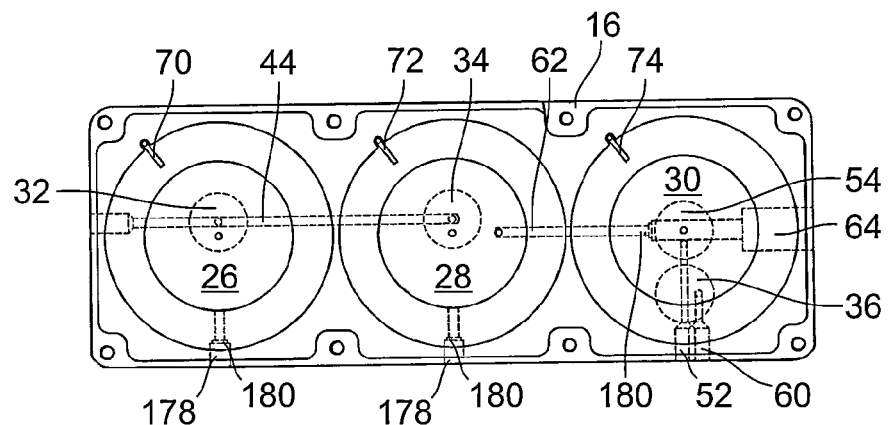
FIG. 2 shows a top view of a container unit shown in FIG. 1.
Figure 3:
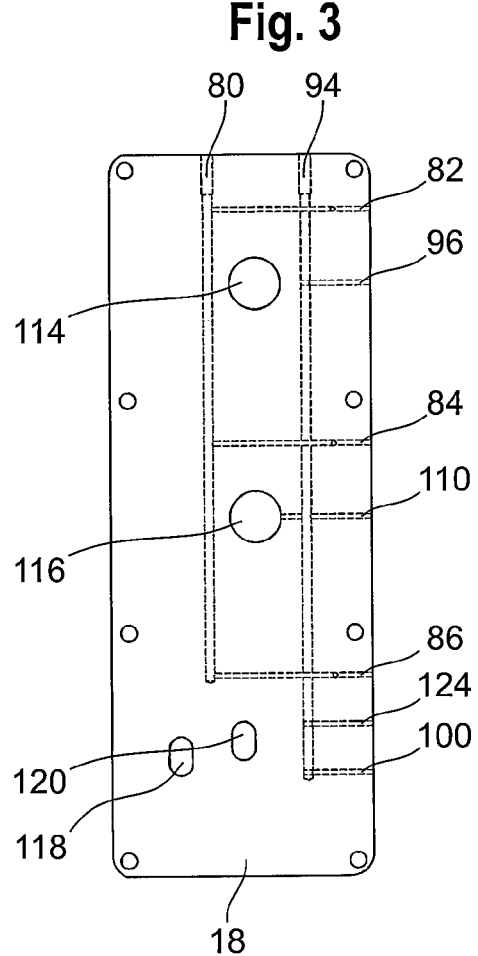
FIG. 3 shows a top view of the valve carrier plate shown in FIG. 1.

New or additional liquid or pharmacological substance is supplied into the respective container 26, 28 via syringes, see the inlets 178 in FIG. 2.

For this purpose, the respective container 26, 28 can have its own supply membrane or the like, which can be pierced by a syringe, but after withdrawing the syringe automatically closes again, which only is an exemplary embodiment.

It is expedient when check valves 180 are present at the inlets 178 and/or in the overflow line 62, as shown in FIG. 2.

A certain difference in height between the test container 10 and the containers 26, 28 can of course also influence the flow.

The invention claimed is:

1. A micro fluid dosing unit for use with a test container containing a biomaterial needing oxygen, the micro fluid dosing unit comprising:
   a one-piece common valve carrier plate, the common valve carrier plate comprising:
      control channels; and
      control channel ports, each control channel port being communicatively coupled with a corresponding control channel and configured to be coupled with at least one control valve of a plurality of control valves;
   a first container configured to contain water, the first container being mounted on the common valve carrier plate;
   a second container configured to contain a pharmacological substance, the second container being mounted on the common valve carrier plate; and
   a common membrane between the first and second containers and the valve carrier plate,
   wherein
      the first and the second containers each have a container outlet configured to be coupled with the test container,
      the common valve carrier plate includes a separate valve control chamber for each of the first and second containers,
      each valve control chamber is sealed by the common membrane, and
      the common membrane is configured to be moved to cause one or more of the container outlets of the first and second containers to be opened and closed by a movement of the common membrane.

2. The micro fluid dosing unit according to claim 1, further comprising:
   a third container configured to receive a recycling liquid, the third contained being mounted on the common valve carrier plate,
   wherein
      the common valve carrier plate includes a separate valve control chamber associated with the third container actuatable by at least one corresponding control valve of the plurality of control valves,
      the separate valve control chamber associated with the third container is sealed by the common membrane, and
      the third container has a corresponding container outlet configured to be opened and closed by the movement of the common membrane.

3. The micro fluid dosing unit according to claim 2, further comprising:
   a return line configured to couple the third container with the test container,
   wherein the common valve carrier plate includes a separate valve control chamber associated with the return line.

4. The micro fluid dosing unit according to claim 2, further comprising:
   an overflow line coupling the third container with the second container.

5. The micro fluid dosing unit according to claim 1, wherein at least the first and second containers are accommodated in a common housing.

6. The micro fluid dosing unit according to claim 5, wherein each of the first and second containers has at least one corresponding distributor chamber in the common housing, and a sidewall of the common housing is configured to be a valve seat against which the common membrane is configured to rest in a closed position.

7. The micro fluid dosing unit according to claim 6, further comprising:
   a common outlet channel coupling the distributor chambers of the first and the second containers,
   wherein the container outlets of the first and second containers are configured to be coupled with the test container by way of the distributor chambers of the first and second containers and the common outlet channel.

8. The micro fluid dosing unit according to claim 1, further comprising:
   separate compressed gas control lines individually coupled with each of the first and second containers; and
   a separate control valve of the plurality of control valves is associated with each compressed gas control line,
   wherein
      each of the first and second containers is closed on an upper side thereof, and
      each separate control valve of the plurality of control valves associated with each compressed gas control line is configured to be opened or closed to cause a compressed gas to be supplied into the associated first or second container.

9. The micro fluid dosing unit according to claim 8, wherein at least one of the separate compressed gas control lines is coupled with the corresponding first or second container in a region of the corresponding first or second container nearer to the upper side of the corresponding first or second container than to a lower side of the corresponding first or second container.

10. The micro fluid dosing unit according to claim 8, wherein the common valve carrier plate includes a compressed gas control channel associated with at least one of the compressed gas control lines, and the compressed gas control channel is configured to be coupled with at least one of the separate control valves of the plurality of control valves associated with each compressed gas control line.

11. The micro fluid dosing unit according to claim 10, wherein the common valve carrier plate includes at least one compressed gas control port communicatively coupled with at least one corresponding compressed gas control channel, and the compressed gas control port is configured to be coupled with the at least one of the separate control valves of the plurality of control valves associated with each compressed gas control line.

12. The micro fluid dosing unit according to claim 8, wherein the common valve carrier plate includes a common compressed gas supply line configured to be communicatively coupled with at least one proportional valve configured to control a flow rate of the compressed gas supplied to at least one of the first or second containers.

13. The micro fluid dosing unit according to claim 12, wherein the at least one proportional valve is a common proportional valve configured to control the flow rate of the compressed gas flowing to the first and second containers.

14. The micro fluid dosing unit according to claim 12, wherein the common compressed gas supply line is configured to be coupled with a pneumatic compressor configured to provide at least one of the compressed gas or a control air for at least one of the control valves by way of the at least one proportional valve.

15. The micro fluid dosing unit according to claim 14, wherein the pneumatic compressor and the at least one proportional valve are accommodated on or in a pneumatic block sealed from an outside environment by a pneumatic block housing.

16. The micro fluid dosing unit according to claim 1, wherein at least one of the control valves of the plurality of control valves is releasably mounted on the common valve carrier plate.

17. The micro fluid dosing unit according to claim 16, wherein the at least one control valve of the plurality of control valves releasably mounted on the common valve carrier plate is coupled with one or more channels of the common valve carrier plate on an end face of the common valve carrier plate.

18. The micro fluid dosing unit according to claim 1, further comprising:
a first compressed gas control line coupled with the first container; and
a second compressed gas control line coupled with the second container,
wherein each of the first and second compressed gas control lines is configured to facilitate flow of a compressed gas into the corresponding first container or the corresponding second container for processing the water or the pharmacological substance contained in the first container or the second container.

19. A testing device, comprising:
a test container configured to receive a biomaterial needing oxygen; and
a micro fluid dosing unit, the micro fluid dosing unit comprising:
a one-piece common valve carrier plate, the common valve carrier plate comprising:
control channels; and
control channel ports, each control channel port being communicatively coupled with a corresponding control channel and configured to be coupled with at least one control valve of a plurality of control valves;
a first container configured to contain water, the first container being mounted on the common valve carrier plate;
a second container configured to contain a pharmacological substance, the second container being mounted on the common valve carrier plate; and
a common membrane between the first and second containers and the valve carrier plate,
wherein
the first and the second containers each have a container outlet configured to be coupled with the test container,
the common valve carrier plate includes a separate valve control chamber for each of the first and second containers,
each valve control chamber is sealed by the common membrane,
the common membrane is configured to be moved to cause one or more of the container outlets of the first and second containers to be opened and closed by a movement of the common membrane, and
the micro fluid dosing unit and the test container are configured to cause fluid to flow between the micro fluid dosing unit and the test container without use of a pump.

* * * * *